(12) United States Patent
Koh et al.

(10) Patent No.: US 7,767,832 B2
(45) Date of Patent: Aug. 3, 2010

(54) METHOD FOR SEPARATING OF OPTICALLY PURE THIOPHENE COMPOUNDS USING SIMULATED MOVING BED CHROMATOGRAPHY

(75) Inventors: Jae Suk Koh, Daejeon (KR); Chun Young Kim, Daejeon (KR); Byoung In Lee, Daejeon (KR); Sang Soo Lee, Daejeon (KR); Seong Jun Lee, Daejeon (KR); Jong Ho Lim, Daejeon (KR); Seon Yeong Jeon, Daejeon (KR); Jun Bae Hong, Daejeon (KR)

(73) Assignee: SK Holdings Co., Ltd., Seoul (KR)

( * ) Notice: Subject to any disclaimer, the term of this patent is extended or adjusted under 35 U.S.C. 154(b) by 443 days.

(21) Appl. No.: 11/721,366

(22) PCT Filed: Dec. 20, 2004

(86) PCT No.: PCT/KR2004/003358

§ 371 (c)(1),
(2), (4) Date: Jun. 11, 2007

(87) PCT Pub. No.: WO2006/068333

PCT Pub. Date: Jun. 29, 2006

(65) Prior Publication Data

US 2009/0234140 A1    Sep. 17, 2009

(51) Int. Cl.
*C07D 495/06* (2006.01)
(52) U.S. Cl. ....................................................... 549/23
(58) Field of Classification Search ................. 549/23
See application file for complete search history.

(56) References Cited

U.S. PATENT DOCUMENTS

| | | | |
|---|---|---|---|
| 4,797,413 A | 1/1989 | Baldwin et al. | |
| 4,968,814 A | 11/1990 | Blacklock et al. | |
| 4,968,815 A | 11/1990 | Blacklock et al. | |
| 5,498,752 A * | 3/1996 | Negawa et al. | 560/249 |
| 5,760,249 A | 6/1998 | Mathre et al. | |

FOREIGN PATENT DOCUMENTS

| | | |
|---|---|---|
| EP | 296879 | 12/1988 |
| EP | 453288 | 10/1991 |
| EP | 0719749 | 7/1996 |

OTHER PUBLICATIONS

Miller et al, J. Chromatography A, vol. 865 (1999) pp. 211-226.*
Tempkin et al., "B-Butyrolactone as a chiral building block in organic synthesis: a convenient synthesis of MK-0507 keto sulfone," Tetrahedron: Asymmetry, 7(9), pp. 2721-2724 (1996).
Pedeferri et al., "Experimental Analysis of a Chiral Separation Through Simulated Moving Bed Chromatography," Chemical Engineering Science, vol. 54, pp. 3735-3748 (1999).
Blacklock et al., "An Enantioselective Synthesis of the Topically-Active Carbonic Anhydrase Inhibitor MK-0507: 5,6-Dihydro-(S)-4-)ethylamino)-(S)-6-methyl-4H-thieno[2,3-b]thiopyran-2-sulfonamide 7,7-Dioxide Hydrochloride," J. Org. Chem., vol. 58, pp. 1672-1679 (1993).

* cited by examiner

*Primary Examiner*—Taofiq A Solola
(74) *Attorney, Agent, or Firm*—McDermott Will & Emery LLP

(57) ABSTRACT

Disclosed herein is a method of producing an optically active thiophene-based compound using a simulated moving bed adsorption separation process, and more specifically, a method of continuously separating a racemic thiophene-based compound into its optically active thiophene-based compounds having high purity, through optical resolution using the simulated moving bed process. According to the method of the current invention, a racemic mixture of a thiophene-based compound can be continuously separated into its optically active thiophene-based compounds having high purity, which is an intermediate of optically active dorzolamide acting as a topical therapeutic agent for glaucoma, using a simulated moving bed adsorption separation technique, thereby increasing industrial usability.

12 Claims, No Drawings

METHOD FOR SEPARATING OF OPTICALLY PURE THIOPHENE COMPOUNDS USING SIMULATED MOVING BED CHROMATOGRAPHY

CROSS REFERENCE TO PRIOR RELATED APPLICATIONS

This application is a U.S. national phase application under 35 U.S.C. §371 of International Patent Application No. PCT/KR2004/003358 filed Dec. 20, 2004 claiming the benefit thereof. The International Application was published in English on Jun. 29, 2006 as International Publication WO 2006/068333 A1 under PCT Article 21(2).

TECHNICAL FIELD

The present invention relates to a method for separating optically pure thiophene-based compounds using a continuous simulated moving bed (SMB) chromatography. More specifically, the present invention is directed to a method for continuously producing an intermediate of dorzolamide with highly pure optical activity, by separation of racemic mixtures of thiophene-based compounds using an SMB adsorption separation process.

BACKGROUND ART

Generally, an SMB adsorption separation process is well known as a technique which has been steadily developed since it was invented by the UOP Company in the 1960s and commercially applied to industrial-scale separations of various isomers in petrochemical processes. Further, the SMB technique has been widely employed in the industry fields concerned with pharmaceuticals and fine chemicals, as diverse chiral stationary phases are developed for use in separation of chiral compounds from the mid 1990s (G. Subramanian, Chiral Separation Techniques, Wiley-VCH, 2000).

The SMB adsorption process is carried out in four zones of desorption, purification, adsorption, and buffering, in which a feed injection port, an eluent injection port, an extract port and a raffinate port are provided between two neighboring zones. Moreover, the SMB process is designed to simulate a countercurrent flow of a fluid relative to a stationary phase by periodically switching the ports in the same direction as fluid flow. Hence, when compared to conventional techniques including enzymatic resolution, asymmetric synthesis, etc., the SMB process is advantageous because both (R)- and (S)-isomers can be simultaneously produced with high purities, and all the process operation conditions required for production of the two isomers having high purity are theoretically found (M. P. Pedeferri, Experimental analysis of a chiral separation through simulated moving bed chromatography, Chemical Engineering Science, vol. 54, 3735-3748, 1999).

In addition, the SMB separation process is reported to have the advantages of continuous operation, and easy recovery of solvent, resulting in higher productivity and a dramatic reduction in solvent consumption, compared to any conventional batch chromatography (R. M. Nicoud, The separation of optical isomers by Simulated Moving Bed Chromatography, Pharmaceutical Technology Europe, March-April, 1999).

Meanwhile, optically active thiophene-based compounds are fundamental materials which play an important role in the preparation of various pharmaceuticals. Particularly, dorzolamide developed by Merck & Co. is a very effective therapeutic agent for the treatment of glaucoma. Hence, methods of efficiently producing optically active thiophene-based compounds, in particular, dorzolamide and an intermediate thereof, are urgently required.

In this regard, the conventional methods of preparing optically active dorzolamide and an intermediate thereof are exemplified as follows:

U.S. Pat. No. 4,968,814 and J. Org. Chem. 1993, 58(7), 1672. disclose a method for preparing an intermediate of dorzolamide that is optically active, by reacting (R)-hydroxybutyric acid methyl ester used as a starting material with thiophene-2-thiol. The disclosed method is advantageous because it uses (R)-hydroxybutyric acid methyl ester having very high optical purity, obtained by the reaction of natural polymer with methanol. However, this method is disadvantageous because an additional chemical reaction is required to react the aforementioned starting material with thiophene-2-thiol, and also, the optical purity of the product is decreased by at least 2% compared to that of the starting material after the reaction with thiophene-2-thiol. Moreover, this method involves multiple reaction steps and the reaction conditions to be precisely controlled or adjusted, and thus, it is unsuitable for use in industrial-scale production.

Likewise, U.S. Pat. No. 4,968,815 discloses a method of preparing an intermediate of dorzolamide that is optically active, using optically active lactone. However, this method also has drawbacks, such as requiring the additional preparation of lactone, and reacting unstably. Therefore, the above method is not suitable for use in industrial-scale production.

Also, U.S. Pat. No. 4,797,413 and EP 0 296 879 B1 disclose a method of preparing optically active dorzolamide, through optical resolution of racemic trans-dorzolamide using a tartaric acid derivative. According to the above method, tartaric acid and its salts are prepared, recrystallized to increase optical purity, and then neutralized, to obtain a final product. The above method is disadvantageous because it requires somewhat complicated processes, and has relatively low yield and optical purity, resulting in being unsuitable for use in industrial-scale production.

DISCLOSURE

Technical Problem

Leading to the present invention, intensive and thorough research into the production of optically active thiophene-based compounds, carried out by the present inventors aiming to avoid the problems encountered in the related prior arts, resulted in the finding that an SMB adsorption separation technique may be applied, whereby a racemic mixture of a thiophene-based compound can be separated into its optically active thiophene-based compounds, in particular, an intermediate of dorzolamide, and also, the intermediate of dorzolamide can be continuously produced with an optical purity as high as 97% ee or more, and a high yield, to the extent of being industrially usable.

Technical Solution

Accordingly, an object of the present invention is to provide a method of separating a racemic mixture of a thiophene-based compound into its optically active thiophene-based compounds having high optical purity while being industrially usable.

In order to accomplish the aforesaid object, the present invention provides a method for separating optically active thiophene-based compounds, comprising continuously separating a thiophene-based racemic mixture represented by the following Formula 1 into (S)-thiophene-based compound and (R)-thiophene-based compound, respectively, which have optical activity, through optical resolution by a simulated moving bed (SMB) adsorption separation process in which an eluent is selected from the group consisting of a polar solvent, mixtures of polar solvents, and mixtures of polar and non-polar solvents, and an adsorbent comprises a support coated with a polysaccharide derivative:

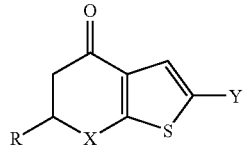

Formula 1

Wherein, X is S or $SO_2$,

Y is H, $SO_3H$ (sulfonic acid), or $SO_2NH_2$ (sulfonamide), and

R is a linear or branched, saturated or unsaturated carbon chain having 1-20 carbons, a saturated or unsaturated carbon ring having 3-20 carbons, or a carbon chain or carbon ring containing a benzene ring having 6-20 carbons.

ADVANTAGEOUS EFFECTS

According to the present invention, it is provided a method for separating a thiophene-based racemic mixture into (S)-thiophene-based compound and/or (R)-thiophene-based compound, in particular, an intermediate of optically active dorzolamide serving as a topical therapeutic agent for glaucoma. Compared with the conventional techniques, the method of the present invention is advantageous because the above isomers can be simultaneously recovered at high yields and high optical purities through a simple separation mechanism without requiring multiple chemical reaction steps. When either (S)-thiophene-based compound or (R)-thiophene-based compound is recovered, an optical purity of 99% ee or more can be achieved. Even when respective optical isomers are simultaneously recovered, an optical purity of 97% ee or more can be achieved. As well, in the case that only one optical isomer is recovered, the untargeted isomer may be racemized and reused, thus minimizing the amount of wastes.

Such racemization can be readily performed using a small amount of a basic material. According to the present invention, it is possible to continuously separate and recover (S)-thiophene-based compound and/or (R)-thiophene-based compound. Further, since the inventive method, which is highly productive per unit time, is environmentally friendly and can economically produce an optically active thiophene-based compound having high purity, in particular, an intermediate of optically active dorzolamide, it is expected to be industrially applicable.

BEST MODE

Hereinafter, a detailed description will be given of the present invention.

As mentioned above, the present invention provides a method for separating a thiophene-based compound (in the form of racemic mixture) into its optically active thiophene-based compounds, in particular, an intermediate of dorzolamide with high optical purity for use as a topical therapeutic agent for glaucoma, through optical resolution using the SMB.

The present method which employs a thiophene-based racemic compound as a starting material is advantageous because it involves simpler reaction processes and uses the readily purchasable inexpensive material, thus it easily produces the target compound, compared to methods of directly synthesizing optically active thiophene-based compounds. Hence, the method of separating the thiophene-based racemic compound used as a starting material into the respective optically active thiophene-based compounds generates various advantages in the aspect of economy and process.

As is apparent from the following Scheme 1, a racemic mixture of a thiophene-based compound along with an eluent is passed through SMB equipment charged with an adsorbent and thus optically resolved, to continuously produce (S)-thiophene-based compound (a) and (R)-thiophene-based compound (b), each of which has optical purity of 97% ee or more.

Scheme 1

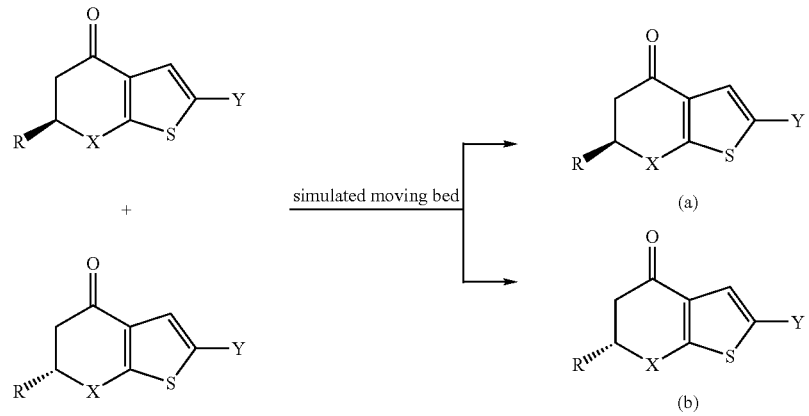

Wherein, X is S or $SO_2$,

Y is H, $SO_3H$, or $SO_2NH_2$, and

R is a linear or branched, saturated or unsaturated carbon chain having 1-20 carbons, a saturated or unsaturated carbon ring having 3-20 carbons, or a carbon chain or carbon ring containing a benzene ring having 6-20 carbons.

As such, the adsorbent used in the SMB equipment comprises a support physically coated with a polysaccharide derivative as chiral selector. Examples of the polysaccharide derivative include chemically modified amylose or cellulose derivatives, and preferably, amylose derivatives, in which a subgroup attached to the derivative includes, for example, carbamate, and preferably, 3,5-dimethylphenylcarbamate or (S)-α-methylbenzylcarbamate. Also, examples of the support includes porous inorganic oxides, and preferably, silica, and more preferably, spherical silica having a particle diameter of about 5-50 μm and an average pore size of about 1 nm to 10 μm. As such, the support is not limited to specific forms, and thus may be used in the forms of extrudate, tablets or granules that are known in the art.

According to the present invention, an eluent suitable for the SMB adsorption separation process may be a polar solvent alone or mixtures thereof, or mixtures of polar and non-polar solvents. Typically, the eluent is exemplified by methanol, acetonitrile, mixtures of acetonitrile and alcohol, and mixtures of alkane and alcohol. Preferably, the eluent is methanol, acetonitrile, a mixture of acetonitrile and methanol, a mixture of acetonitrile and ethanol, a mixture of acetonitrile and isopropanol, a mixture of n-hexane and isopropanol, a mixture of n-hexane and ethanol, a mixture of isohexane and isopropanol, a mixture of isohexane and ethanol, a mixture of heptane and isopropanol, or a mixture of heptane and ethanol. More preferably, the eluent is a mixture of acetonitrile and isopropanol, which has a volumetric ratio of about 80:20 to about 98:2.

In the present invention, the adsorption separation performance may be affected by various process conditions. Preferably, the temperature for the adsorption separation process is in the range of about 10-40° C., and preferably, about 30-40° C. If the separation temperature is too low, desorption efficiency becomes problematic. On the other hand, if the above temperature is too high, the polysaccharide derivative coated onto the support may be detached therefrom or expanded, thus losing the separation ability. In addition, the pressure may be controlled in the range of not negatively affecting the extent of separation, for example, about 1-50 bar.

As described above, when compared with the conventional techniques, the present method of separating (S)-thiophene-based compound and/or (R)-thiophene-based compound is advantageous because the respective isomers can be simultaneously recovered at high yields and high optical purities through a simple separation mechanism, without requiring complicated multiple chemical reaction steps.

As well, in the case of recovering either (S)-thiophene-based compound or (R)-thiophene-based compound, an optical purity of 99% ee or more can be achieved. Further, in the case that the two optical isomers are simultaneously separated and recovered at high purities, they can have optical purities of 97% ee or more.

Meanwhile, in the case that only the isomer having specific optical activity is recovered, an undesired (that is, non-recovered) optical isomer can be racemized to be reused as a material for optical resolution, thus minimizing the amount of wastes. The racemization may be performed using about 0.001-1 equivalents of basic material based on the amount of reactant. Specifically, the basic material may be lithium hydroxide, sodium hydroxide, potassium hydroxide, cesium hydroxide, barium hydroxide, magnesium hydroxide, calcium hydroxide, sodium bicarbonate, potassium bicarbonate, lithium carbonate, sodium carbonate, potassium carbonate, ammonia, organic amine compounds including methylamine, ethylamine, propylamine, butylamine, pyrrolidine, piperidine, piperazine, pyrrole, and pyridine, or combinations thereof, and the selected basic material is added to the non-recovered optical isomer to effect the racemization.

According to the method of the present invention, it is possible to continuously produce (S)-thiophene-based compound or (R)-thiophene-based compound. Further, productivity per unit time is very high, and thus, the method of the present invention is environmentally friendly and economical, and can be industrially applied.

MODE FOR INVENTION

A better understanding of the present invention may be obtained through the following examples which are set forth to illustrate, but are not to be construed as the limit of the present invention.

Example 1

Separation of (S)-5,6-dihydro-6-methylthieno[2,3-b]thiopyran-4-one of Formula 2

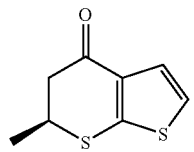

Formula 2

To evaluate the applicability of (S)-5,6-dihydro-6-methylthieno[2,3-b]thiopyran-4-one to an SMB adsorption separation technique, liquid chromatography was performed, using an adsorbent (ChiralPak AD adsorbent having a particle diameter of 20 μm and being in spherical form, Daicel Chemical Industries, LTD) composed of silica gel coated with an amylose derivative as chiral selector in which hydrogen of a hydroxy group of amylose was replaced by 3,5-dimethylphenylcarbamate, and pure methanol as a solvent. The separation column had an inner diameter of 1 cm and a length of 10 cm, the separation temperature was 35° C., and the flow rate of the solvent was 1.5 ml/min. As the experimental result, a high selectivity of 1.8 was obtained.

Example 2

Racemization of (R)-5,6-dihydro-6-methylthieno[2,3-b]thiopyran-4-one 5 g (27.2 mmol) of (R)-5,6-dihydro-6-methylthieno[2,3-b]thiopyran-4-one having 99% ee, separated using the SMB adsorption separation technique, was dissolved in 10 ml of methanol, and then added with 0.38 g (2.7 mmol) of potassium carbonate dissolved in 5 ml of water. The reaction mixture was stirred for 6 hours and refluxed, and then confirmed by chiral HPLC. As a result, the title compound was found to be 0% ee.

Example 3

Separation of (S)-5,6-dihydro-6-methyl-7,7-di-oxothieno[2,3-b]thiopyran-4-one of Formula 3

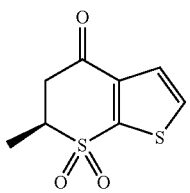

Formula 3

To evaluate the applicability of (S)-5,6-dihydro-6-methyl-7,7-dioxothieno[2,3-b]thiopyran-4-one to an SMB adsorption separation technique, liquid chromatography was performed, using an adsorbent (ChiralPak AD adsorbent having a particle diameter of 20 μm and being in spherical form, Daicel Chemical Industries, LTD) composed of silica gel coated with an amylose derivative as chiral selector in which hydrogen of a hydroxy group of amylose was replaced by 3,5-dimethylphenylcarbamate, and a mixture of acetonitrile and isopropanol mixed at a volumetric ratio of 95:5 as a solvent. The separation column had an inner diameter of 1 cm and a length of 10 cm, the separation temperature was 30° C., and the flow rate of the solvent was 1.5 ml/min. As the experimental result, the retention times of two optical isomers were found to be 4.4 min and 7.2 min, respectively, and a very high selectivity of 4.8 was obtained.

Example 4

Continuous Separation of (S)-5,6-dihydro-6-methyl-7,7-dioxothieno[2,3-b]thiopyran-4-one and (R)-5,6-dihydro-6-methyl-7,7-dioxothieno[2,3-b]thiopyran-4-one A complete separation condition of an SMB adsorption separation process was determined by an overloading experiment of the sample using liquid chromatography, which was verified using a laboratory-scale SMB unit. The above unit was equipped with 8 columns (ChiralPak AD) each having an inner diameter of 1 cm and a length of 10 cm, in which a mixture of acetonitrile and isopropanol mixed at a volumetric ratio of 95:5 was used as a solvent. Thereby, either (R)-isomer or (S)-isomer was produced at 99% ee. Also, in cases that the above isomers were simultaneously produced at high purities, each isomer could have 97% ee. Further, from simulation based on the above results, high productivity of about 4.5 kg/kg CSP/day (4.5 kg of each optical isomer can be produced upon one day operation in the case of using an SMB unit filled with 1 kg of a stationary phase) was predicted.

Example 5

Racemization of (R)-5,6-dihydro-6-methyl-7,7-di-oxothieno[2,3-b]thiopyran-4-one 5 g (23.1 mmol) of (R)-5,6-dihydro-6-methyl-7,7-dioxothieno[2,3-b]thiopyran-4-one having 99% ee, separated by the SMB adsorption separation technique, was dissolved in 1 ml of methanol, and then 0.32 g (2.3 mmol) of potassium carbonate dissolved in 5 ml of water was added. The reaction mixture was stirred at room temperature for 3 hours, and confirmed by chiral HPLC. As the result, the title compound was found to be 0% ee.

INDUSTRIAL APPLICABILITY

As described above, the present invention provides a method of separating a thiophene-based racemic compound into (S)-thiophene-based compound or (R)-thiophene-based compound, in particular, an intermediate of optically active dorzolamide serving as a topical therapeutic agent for glaucoma. Compared to the conventional techniques, the method of the present invention is advantageous because the above isomers can be simultaneously obtained at high yields and high optical purity through a simple separation mechanism without requiring multiple chemical reaction steps. When either (S)-thiophene-based compound or (R)-thiophene-based compound is recovered, optical purity of 99% ee or more can be achieved. Also, when the two optical isomers are simultaneously recovered, optical purity of 97% ee or more can be achieved. As well, in the case where only one optical isomer is recovered, the undesired isomer may be racemized and recycled, thus minimizing the amount of waste. The racemization may be easily performed using a small amount of base. According to the method of the present invention, it is possible to continuously separate and recover (S)-thiophene-based compound and/or (R)-thiophene-based compound. Further, since the novel method, which generates high productivity per unit time, is environmentally friendly and can economically produce the thiophene-based compound with highly pure optical activity, in particular, the intermediate of optically active dorzolamide, it is expected to be industrially usable.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for separating an optically active thiophene-based compound, which comprises continuously separating a thiophene-based racemic mixture represented by the following Formula 1 into (S)-thiophene-based compound and (R)-thiophene-based compound, respectively, through optical resolution by a simulated moving bed (SMB) adsorption separation process in which an eluent is a mixture of acetonitrile and isopropanol, and an adsorbent comprises a support coated with a polysaccharide derivative:

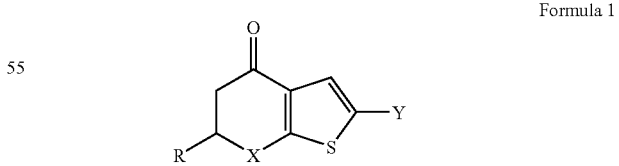

Formula 1

Wherein, X is S or $SO_2$,

Y is H, $SO_3H$, or $SO_2NH_2$, and

R is a linear or branched, saturated or unsaturated carbon chain having 1-20 carbons, a saturated or unsaturated carbon ring having 3-20 carbons, or a carbon chain or carbon ring containing a benzene ring having 6-20 carbons.

2. The method according to claim 1, wherein the polysaccharide derivative is an amylose or cellulose derivative.

3. The method according to claim 2, wherein the polysaccharide derivative is an amylose derivative having a subgroup of 3,5-dimethylphenylcarbamate or (S)-α-amethylbenzylcarbamate.

4. The method according to claim 1, wherein the support is silica.

5. The method according to claim 4, wherein the silica support is a spherical silica having a particle diameter of 1-50 μm, and an average pore size of 1 nm to 10 μm.

6. The method according to claim 1, wherein the mixture of acetonitrile and isopropanol has a volumetric ratio of 80:20-98:2.

7. The method according to claim 1, wherein the separating is performed in a temperature range of 10-40° C.

8. The method according to claim 7, wherein the separating is performed in a pressure range of 1-50 bar.

9. The method according to claim 1, further comprising recovering either (S)-thiophene-based compound or (R)-thiophene-based compound, in which the recovered optical isomer of the thiophene-based compound has an optical purity of 99% ee or more.

10. The method according to claim 9, further comprising racemizing the non-recovered optical isomer of the thiophene-based compound to reuse as a material for the optical resolution.

11. The method according to claim 10, wherein the racemizing step is performed by adding a basic material to the non-recovered optical isomer of the thiophene-based compound, the basic material being selected from the group consisting of lithium hydroxide, sodium hydroxide, potassium hydroxide, cesium hydroxide, barium hydroxide, magnesium hydroxide, calcium hydroxide, sodium bicarbonate, potassium bicarbonate, lithium carbonate, sodium carbonate, potassium carbonate, ammonia, organic amine compounds including methylamine, ethylamine, propylamine, butylamine, pyrrolidine, piperidine, piperazine, pyrrole, and pyridine, and combinations thereof.

12. The method according to claim 1, further comprising recovering both of the respectively separated (S)-thiophene-based compound and (R)-thiophene-based compound, in which each of the two recovered optical isomers has an optical purity of 97% ee or more.

* * * * *